US009393343B2

(12) United States Patent
Im et al.

(10) Patent No.: US 9,393,343 B2
(45) Date of Patent: Jul. 19, 2016

(54) MONOFILAMENT SUTURE AND PREPARATION METHOD THEREOF

(75) Inventors: Jung-Nam Im, Daejeon (KR);
Jeong-Kyung Kim, Daejeon (KR);
Tae-Hun Kim, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 1770 days.

(21) Appl. No.: 11/721,374

(22) PCT Filed: Dec. 23, 2005

(86) PCT No.: PCT/KR2005/004507
§ 371 (c)(1),
(2), (4) Date: Jun. 11, 2007

(87) PCT Pub. No.: WO2006/071032
PCT Pub. Date: Jul. 6, 2006

(65) Prior Publication Data
US 2009/0275979 A1    Nov. 5, 2009

(30) Foreign Application Priority Data
Dec. 29, 2004  (KR) .................. 10-2004-0115444
Dec. 23, 2005  (KR) .................. 10-2005-0128534

(51) Int. Cl.
*A61B 17/06* (2006.01)
*A61L 17/10* (2006.01)
(Continued)

(52) U.S. Cl.
CPC ........... *A61L 17/10* (2013.01); *A61B 17/06166* (2013.01); *A61L 17/04* (2013.01); *D01F 8/04* (2013.01); *A61B 2017/00526* (2013.01)

(58) Field of Classification Search
CPC ............... A61B 17/06166; A61B 2017/00526; D01F 8/04; D01D 5/36
USPC .................. 606/228–230; 428/357–401, 212; 264/172.13
See application file for complete search history.

(56) References Cited

U.S. PATENT DOCUMENTS 4,008,344 A * 2/1977 Okamoto et al. ............. 428/374
4,601,949 A * 7/1986 Bach et al. .................... 428/374
(Continued)

FOREIGN PATENT DOCUMENTS

EP      1348449 A    10/2003
JP      03080868 A    4/1991
(Continued)

OTHER PUBLICATIONS

Van Rijssel EJC, et al., Mechanical performance of square knots and sliding knots in surgery: A comparative study, Am J Obstet Gynecol, Jan. 1990; 162:93-7.
(Continued)

*Primary Examiner* — Alexander Orkin
(74) *Attorney, Agent, or Firm* — Lex IP Meister, PLLC

(57) ABSTRACT

The present invention relates to a monofilament suture and a preparation method thereof, more specifically, to a novel monofilament suture wherein two polymers having identical inherent properties are spun to have a cross-sectional structure of conjugated filaments, and said cross-section has interfaces between the spun polymers. The interfaces form a discontinuous cross-section along the radial direction and are distributed continuously along the fiber axis direction, thereby offering improved knot security and applicability to a variety of medical materials, and a preparation method thereof.

9 Claims, 4 Drawing Sheets

(51) Int. Cl.
*A61L 17/04* (2006.01)
*D01F 8/04* (2006.01)
*A61B 17/00* (2006.01)

(56) References Cited

U.S. PATENT DOCUMENTS

| | | | |
|---|---|---|---|
| 4,713,291 A * | 12/1987 | Sasaki et al. | 428/373 |
| 5,059,630 A * | 10/1991 | Fujita et al. | 521/61 |
| 5,480,961 A * | 1/1996 | Jiang et al. | 528/220 |
| 5,540,992 A | 7/1996 | Marcher et al. | |
| 5,554,435 A * | 9/1996 | Gupta et al. | 442/346 |
| 5,593,778 A * | 1/1997 | Kondo et al. | 428/373 |
| 5,626,611 A | 5/1997 | Liu et al. | |
| 5,641,501 A | 6/1997 | Cooper et al. | |
| 5,645,936 A * | 7/1997 | Frankfort et al. | 428/395 |
| 5,807,490 A * | 9/1998 | Davis et al. | 210/739 |
| 5,997,568 A | 12/1999 | Liu | |
| 6,045,571 A * | 4/2000 | Hill et al. | 606/228 |
| 6,090,910 A | 7/2000 | Shinoda et al. | |
| 6,093,200 A * | 7/2000 | Liu et al. | 606/228 |
| 6,162,537 A | 12/2000 | Martin et al. | |
| 6,174,603 B1 * | 1/2001 | Berger | 428/373 |
| 6,287,499 B1 * | 9/2001 | Roby et al. | 264/210.5 |
| 6,315,788 B1 | 11/2001 | Roby | |
| 6,624,097 B2 * | 9/2003 | Martin et al. | 442/199 |
| 6,638,456 B2 * | 10/2003 | Klein et al. | 264/103 |
| 7,622,188 B2 * | 11/2009 | Kamiyama et al. | 428/370 |
| 2002/0009938 A1 * | 1/2002 | Katayama et al. | 442/181 |
| 2003/0236553 A1 | 12/2003 | Knudsen | |
| 2007/0196649 A1 * | 8/2007 | Kamiyama et al. | 428/373 |

FOREIGN PATENT DOCUMENTS

| | | |
|---|---|---|
| JP | 10120774 A | 5/1998 |
| KR | 101999010319 A | 2/1999 |

OTHER PUBLICATIONS

Van Rijssel EJC, et al., Tissue reaction and surgical knots: the effect of suture size, knot configuration, and knot volume, Obstet Gynecol, Jul. 1989; 74:64-8.

Trimbos, J. B., Security of various knots commonly used in surgical practice, Obstet Gynecol., 64:274-80, Aug. 1984.

* cited by examiner (a)                  (b)

MONOFILAMENT SUTURE AND PREPARATION METHOD THEREOF

BACKGROUND OF THE INVENTION (a) Field of the Invention

The present invention relates to a monofilament suture and a method to prepare the same. In particular, the present invention relates to a monofilament suture, wherein polymers having identical inherent properties are spun to have a cross-sectional structure of conjugated filaments, and said cross-section has interfaces between the spun polymers, discontinuous in the radial direction of the monofilament and continuously distributed in the axial direction of the monofilament, to improve knot security of the monofilament suture. Therefore, the monofilament suture of the present invention can be applied for various medical uses.

(b) Description of the Related Art

Monofilament sutures generally exhibit less tissue drag and cause less tear because they have smoother surfaces than braided multifilament sutures. Monofilament sutures, in general, do not provide the capillarity found in multifilament sutures, which minimizes the spread of wound infection with bacteria and the like.

However, since monofilament sutures comprise a single filament, there are the following disadvantages: they are less flexible than multifilament sutures; it is more difficult to tie a knot; and the tied knot is more likely to loosen due to inferior knot security.

In addition, even if a marketed monofilament suture is relatively flexible, its knot is easily untied. Therefore, in order to make the knot secure, additional throws while tying are required.

Such additional throws increase the amount of suture remaining inside the body, and, consequently, increase the irritation caused by the foreign material in the wound. This increase in foreign body, even in the case of an absorbable suture with good biocompatibility, may provoke irritation in adjacent tissues, and thus, increase the probability of inflammation. Furthermore, a patient may feel sensations or stimulation from the knots. The larger the volume of tied knots there is, the more likely it is that undesirable symptoms will present. (Van Rijssel EJC, et al., Mechanical performance of square knots and sliding knots in surgery: A comparative study, Am J Obstet Gynecol 1990; 162:93-7, Van Rijssel EJC, et al., Tissue reaction and surgical knots: the effect of suture size, knot configuration, and knot volume, Obstet Gynecol 1989; 74:64-8, Trimbos, J. B., Security of various knots of commonly used in surgical practice, Obstet Gynecol., 64:274-80,1984).

The monofilament is conventionally prepared through single extrusion of single polymer, and in some cases, is prepared through conjugated spinning of different polymers.

As a method to prepare a monofilament suture by conjugated spinning, U.S. Pat. Nos. 5,626,611, 6,093,200, 6,315,788, 5,641,501, 6,090,910, 5,997,568, and 6,162,537 disclose a method of performing the conjugated spinning of different polymers, to control the degradation rate of the obtained absorbable suture. These methods of preparing sutures by conjugated spinning of different polymers have an advantage of overcoming the defects present in each polymer by using at least two polymers in combination, when compared with the method of preparing the suture by single spinning. However, when using different polymers, the preparation of a suture is difficult, since the melting properties, such as the melting point and the like, are different.

U.S. Pat. Nos. 5,540,992 and 6,093,200 disclose a technique of conjugated spinning using similar but different polymers.

U.S. Pat. No. 5,540,992 discloses a method of preparing a fiber for a non-woven fabric having an improved flexibility by conjugated spinning of high-density polyethylene and low-density polyethylene in sheath/core form using the difference between the melting points. However, although high-density polyethylene and low-density polyethylene have same chemical formula, since the molecular structures thereof are different, that is, one has a linear chain structure and the other has a branched chain structure, the melting properties thereof, such as the melting point, are different, and thus, the processing conditions thereof are also different from each other.

U.S. Pat. No. 6,093,200 discloses a method of preparing a suture by conjugated spinning of two kinds of polypropylene sharing the same chemical formula but having different melting properties due to different stereo-regularity.

As can be seen from the aforementioned related art, up to the present, many studies have been performed on techniques to improve the flexibility and strength of the suture or to control absorption rate.

However, research into improving knot security, as one of the important requirements of a suture, has not been enough. Therefore, the present invention provides a suture with excellent knot security and flexibility, which helps overcome the disadvantages of currently marketed monofilament sutures.

SUMMARY OF THE INVENTION

The present inventors have performed continuous studies to satisfy the above need. As the result thereof, the present inventors found that different from the conventional method of conjugated spinning of at least two polymers having different properties, when polymers having the same inherent properties are spun to have a cross-sectional structure of conjugated filaments, a novel monofilament suture having a cross-section having interface which is discontinuous in the radial direction of the monofilament and continuous in the axial direction of the monofilament can be prepared, and the prepared suture has an improved knot security, to complete the present invention.

Therefore, the object of the present invention is to provide a monofilament suture wherein polymers having the same inherent properties are first used in conjugated spinning, to introduce the advantages of the conventional monofilament suture, and at the same time, to overcome the disadvantages thereof that it is difficult to tie knots. Another object of the present invention is to provide a method of preparing the monofilament suture.

Figure 1:
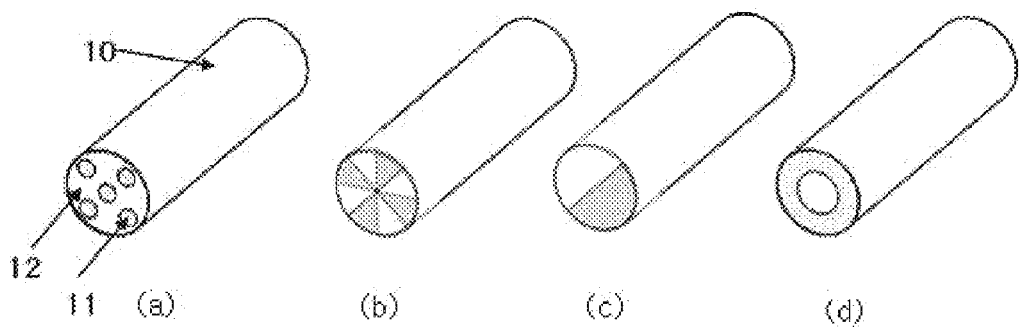
FIG. 1 is a perspective view schematically showing the structure of the monofilament of the present invention, wherein (a) is a sea/island type, (b) is a segmented pie type, (c) is a side-by-side type, and (d) is a sheath/core type.

[Description of the reference numbers used in the Drawings]

| 10: sea/islands type monofilament | |
|---|---|
| 11: islands part | 12: sea part |
| 21: extruder | 22: metering pump |
| 23: spinning block | 24: monofilament spun |
| 25: cooling bath | 26: drawing apparatus |
| 27: winder | 31: distributing plate |
| 32: nozzle | 33 & 34: flow channel |

DETAILED DESCRIPTION OF THE PREFERRED EMBODIMENTS

The present invention relates to a monofilament suture wherein a first polymer and a second polymer that have the identical inherent property are spun into a monofilament having a cross-sectional structure of conjugated filaments and the cross-section has interfaces discontinuously distributing in the radial direction of the cross-section of the monofilament.

In addition, the present invention relates to a method of preparing the monofilament suture, comprising the steps of spinning, solidifying, crystallizing, and drawing to prepare the monofilament, wherein the spinning step is performed by melting a first polymer and a second polymer that have identical inherent properties, and then, spinning into a monofilament having a cross-sectional structure of conjugated filaments.

Hereinafter, the present invention will be described in detail.

The present invention relates to a novel monofilament suture and a method of preparing the same, wherein the monofilament is obtained by spinning of a first polymer and a second polymer which have the identical inherent properties to a cross-sectional structure of conjugated filaments such that the cross-section has interfaces which are discontinuous in the radial direction of the cross-section of the monofilament and continuously distributed in the axial direction of the monofilament. The monofilament suture of the present invention has improved knot security, and so can be applied for various medical uses.

The monofilament suture of the present invention is characterized in that the first polymer and the second polymer which share identical inherent properties are spun into a monofilament having a cross-sectional structure of conjugated filaments and the cross-section has interfaces discontinuously distributing in the radial direction.

The monofilament suture of the present invention is characterized in that the first polymer and the second polymer are identical to each other not only in chemical composition but also in the inherent properties, such as melting point, density, and modulus of elasticity, due to their identical stereoregularity, chain structure, and the like.

The spinning of polymers having identical inherent property using conjugated spinning gives the cross-section having interfaces which are discontinuous along the radial direction. That is, differently from the monofilament having a cross-section continuous in the radial direction obtained by a conventional single spinning, the monofilament of the present invention has a cross-section discontinuous along the radial direction. Further, in the present invention, the spinning of polymers having identical inherent properties divided into the first polymer and the second polymer to have cross-sectional structure of conjugated filaments gives interfaces continuous along the fiber axis direction of the obtained monofilament, which is a different characteristic from the conventional monofilament obtained by a conventional blending method wherein the interfaces are formed discontinuously along the fiber axis direction. This characteristic of the monofilament suture of the present invention can be confirmed by scanning electron microscope (SEM) or optical microscope.

The cross-section of the monofilament suture of the present invention may be of any type with interfaces, as long as the neighboring polymers are discontinuous with each other. To give specific but nonrestrictive examples, the discontinuous cross-section of the monofilament of the present invention may include a sea/islands type, a segmented pie type, a side-by-side type, a sheath/core type, etc. In FIG. 1, a sea/islands type (a), a segmented pie type (b), a side-by-side type (c), and a sheath/core type (d) are illustrated schematically. As shown in FIG. 1, in a monofilament 10 having a sea/islands type cross-section (a), islands 11 are surrounded by a sea 12. In this construction, the islands 11 and the sea 12 are formed from polymers having the identical inherent properties.

In preparation of a suture, a dye may be added in the amount of 0.5 parts by weight or less on the basis of 100 parts by weight of the polymer for convenience in a surgical operation. However, as for the conventional sutures, the dye tends to be bled from the polymer used in the monofilament suture because it is physically mixed with the polymer, rather than chemically bonded to the polymer.

The present invention can solve this problem. For example, by adding a dye more in the islands or core and less or none in the sea or sheath, a colored suture can be obtained, which offers convenience in a surgical operation. Since the suture has no or little dye at the outer part, the possibility of the color bleeding from the suture can be reduced.

The content of the dye, in accordance with the present invention, can be expressed by the following equation.

$$0 \leq \frac{\text{Dye content in the sea or sheath}}{\text{Dye content in the islands or core}} < 1$$

Preferably, a dye may be added only to the islands or core of the suture for better distinction of the interfaces and for minimization of color bleeding. The dye may be any one commonly used in sutures. Preferably, D&C Violet No.2, D&C Blue No. 6 or CU-Phtalocyanine Blue may be used in the amount of 0.5 parts by weight or less on the basis of 100 parts by weight of the polymer.

Also, an accelerating agent for hydrolysis may be added to, or a polymer having a low molecular weight may be mixed with one polymer component of the monofilament, to reduce bioabsorption time while maintaining the physical properties of the suture.

The monofilament suture of the present invention, which is prepared from polymers having identical properties and having a discontinuous cross-section along the radial direction, comprises the first polymer and the second polymer with a proportion from 5:95 to 95:5, preferably from 20:80 to 80:20 by volume. A content of either of the polymers of less than 5 percent by volume is undesirable, because the interface may be indistinct.

The polymers comprised in the monofilament suture of the present invention have the identical inherent properties, and it is more preferable to use the polymers having different melt viscosities. The melt viscosity of the polymer may be different depending on the molecular weight and/or the molecular weight distribution of the polymer or the processing temperatures, such as the temperature of extruder or metering pump, etc., even if the polymer has the identical inherent properties. The flow properties of the polymers may be different due to the difference of the melt viscosity. The melt viscosity may be expressed by melt index.

A monofilament made from polymers with identical inherent properties and different melt viscosities facilitates phase separation at the interface when knotted, thereby increasing the shape deformation during knot tying, resulting in superior knot security. Accordingly, the use of polymers with identical inherent properties and different melting properties, such as the melt viscosity, gives the improved knot security.

Melt viscosities of the polymers may be different depending on the kinds of the polymer and the measuring technique. It is preferable that the difference between the melt viscosities of the first polymer and the second polymer composing the monofilament suture is 10 to 1500%, more preferably 10 to 1000%. If the difference in melt viscosity is larger than the above range, the spinning may be difficult. The melt indices of the polymers used in the present invention are measured at 235° C. in the case of nylon, and in the case of other polymers, melt index is measured at 180° C. under a load of 2.16 kgf after being preheated at 180° C. for 5 minutes.

Either a bioabsorbable polymer or a non-bioabsorbable polymer may be used in the monofilament suture of the present invention. Herein, a bioabsorbable polymer refers to a polymer that can be disintegrated by water or enzymes present in the body to be converted from a high-molecular-weight polymer into a low-molecular-weight polymers, and excreted out of the body after being metabolized.

The bioabsorbable polymer may be a homopolymer or a copolymer of the polymers selected from the group consisting of glycolide, glycolic acid, lactide, lactic acid, ε-caprolactone, p-dioxanone, trimethylene carbonate, polyethylene glycolide, polyanhydride, polyhydroxyalkanoate, and the like.

Preferably, a homopolymer or a copolymer of polydioxanone, a copolymer of polyglycolic acid and polylactide, a homopolymer or a copolymer of polymers selected from the group consisting of polycaprolactone, trimethylene carbonate, polyethylene glycol, DL-polylactide and the like may be used.

A non-bioabsorbable polymer may be a homopolymer or a copolymer of polymers selected from the group consisting of polyolefin, polyamide, polyurethane, polyvinylidene fluoride and the like. In the specific embodiment of the present invention, polypropylene, polyethylene, polyvinylidene fluoride, polyamide, such as nylon 6 and nylon 66, and the like may be used.

The monofilament suture of the present invention has superior knot security. Therefore, it may be used for soft tissue patches, surgical meshes, thin-film type dressings, surgical felts, artificial blood vessels, nerve therapy aids, artificial skins, sternum tapes, and the like, as well as for sutures.

Moreover, in the spinning into the monofilament, the addition of compounds, such as chitosan, silver compounds, and the like, for improving wound healing ability, or the addition of a small amount of polymers and additives for improving knot security and flexibility is understood to be within the scope of the present invention.

Figure 2A:
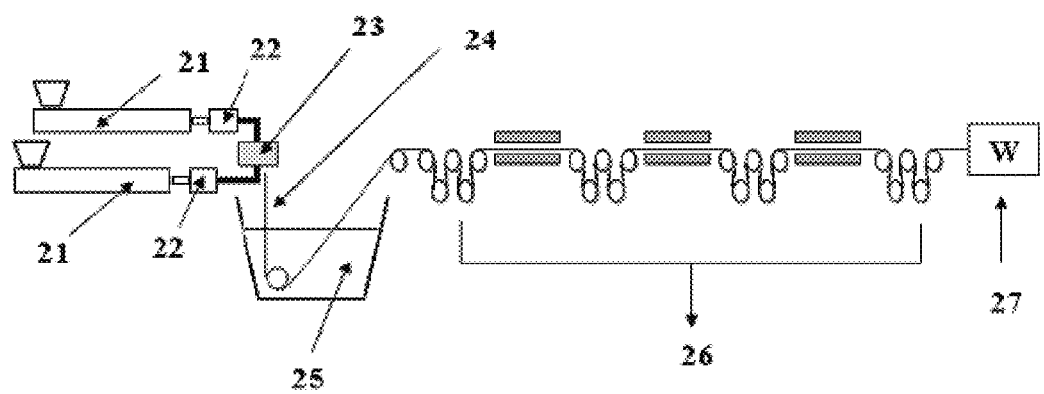
FIGS. 2A and 2B are schematic views showing the spinning process for the monofilament suture of the present invention.

The process of spinning the monofilament suture of the present invention by spinning to have a cross-sectional structure of conjugated filaments is more specifically described with reference to the drawings, as follows:

FIG. 2A schematically illustrates the process of conjugated spinning, which is one of the processes of preparing the monofilament suture of the present invention having interfaces between polymers composing the monofilament. A commonly used conjugated spinning machine is illustrated in the figure. Specifically, two polymers are melted respectively in two extruders 21. The melted first polymer and second polymer are discharged in a desired amount through metering pumps 22. The content ratio of each polymer in the final monofilament suture can be controlled by adjusting the metering pumps 22. The melted polymers discharged through the metering pumps 22 are spun into a monofilament 24 having a cross-sectional structure of conjugated filaments through a spinning block 23. The resulting monofilament 24 is solidified and crystallized in a cooling bath 25. Preferably, the air gap between the outlet of the spinning block 23 and the top surface of water in the cooling bath is 0.5 to 100 cm, more preferably, 1 to 30 cm. The solidified monofilament is drawn through drawing machinery 26 for improving physical properties due to orientation and wound through a winder 27. In order to improve physical properties of the suture, the solidified monofilament may be drawn after aging. For example, the solidified monofilament 24 may be wound from UDT (undrawn yarn) and aged under adequate conditions before drawing, and then, drawn through the drawing machinery 26. Also, the polymers may be annealed under adequate conditions (e.g., 50 to 200° C.) depending on the kind of polymer used in order to improve physical properties thereof.

Figure 2B:
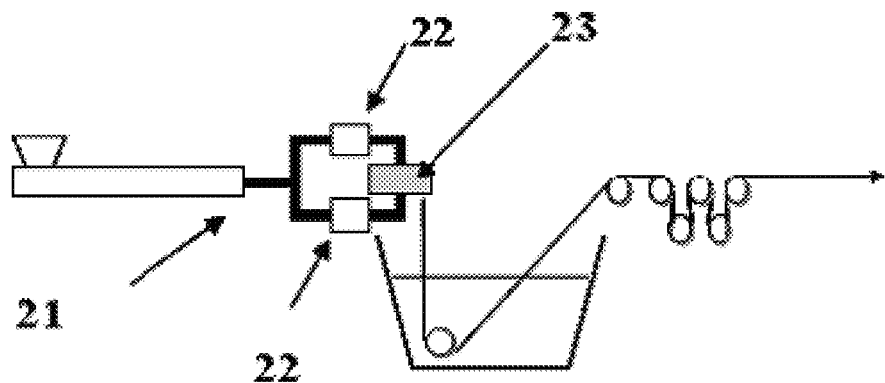

FIG. 2B schematically illustrates a spinning machine modified from the conventional one used for monofilament production, wherein a single extruder 21 used for melting the polymers, two metering pumps 22 and two flow channels connecting the extruder and the metering pumps 22 are equipped to be capable of performing conjugated spinning. The process after a spinning block 23 is the same as in FIG. 2a. Although production of a single strand of monofilament is illustrated in FIG. 2, more than one strand can be produced at the same time, depending on the diameter of the monofilament. The conditions for the spinning and drawing can be determined in accordance with the practices well known in the art.

Figure 3:
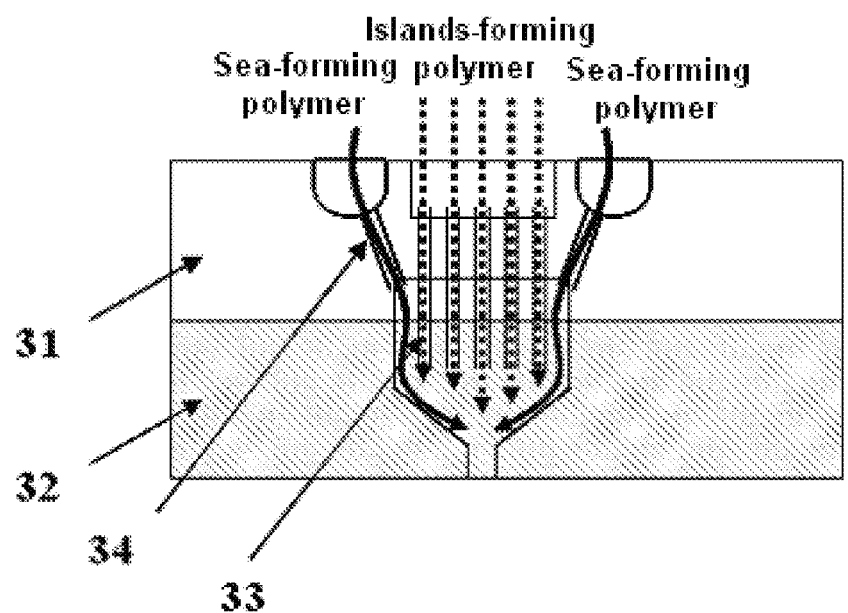
FIG. 3 is a schematic view of the spinning pack (nozzle pack) used in the present invention.

FIG. 3 schematically illustrates an embodiment of a spinning pack comprising a nozzle and a distributing plate, which can be used as the spinning block 23 in the present invention. To take a monofilament having the cross-section of a sea/islands type as an example, each melted polymer flows into a nozzle 32 passing through a distributing plate 31 to form a monofilament. Specifically, FIG. 3 illustrates a spinning pack for preparing a sea/islands type suture, wherein a polymer that forms the islands flows through a plurality of flow channels 33 in a distribution panel 31 for islands formation, and a polymer that forms the sea flows through flow channels 34 in a distribution panel 31 for sea formation and surrounds the polymer forming the islands. The number and arrangement of the flow channels 33 in the distribution plate 31 may be different, depending on the physical properties of the desired final filament.

The monofilament suture of the present invention which is spun from polymers having identical properties to have a cross-sectional structure of conjugated filaments has a cross-section with interfaces between the polymers like conjugated filaments (FIG. 4a). Further, it has improved knot security compared with those prepared by single spinning of a single polymer.

Figure 5A:
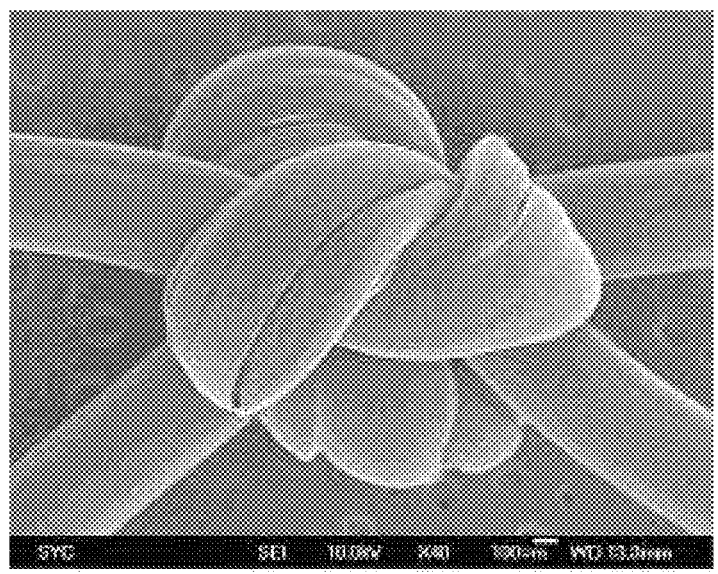
FIG. 5A is an SEM image showing the shape of the tied knot of the monofilament suture prepared in Example 1.

During knot tying, a normal force is applied at the direction perpendicular to the length direction of the monofilament. Therefore, in a monofilament produced by spinning into a monofilament having a cross-sectional structure of conjugated filament according to the present invention, and shape deformation, such as 'hills and valleys', are easily generated due to cracks at the knotted site under normal force, to increase the friction coefficient of surface, resulting in improving the knot security, even when polymers having identical inherent properties are used. That is, as shown in FIG. 5A, the monofilament suture of the present invention is deformed during knot tying, for example by hills and valleys, to significantly improve the friction coefficient at the knotted site.

Figure 5B:
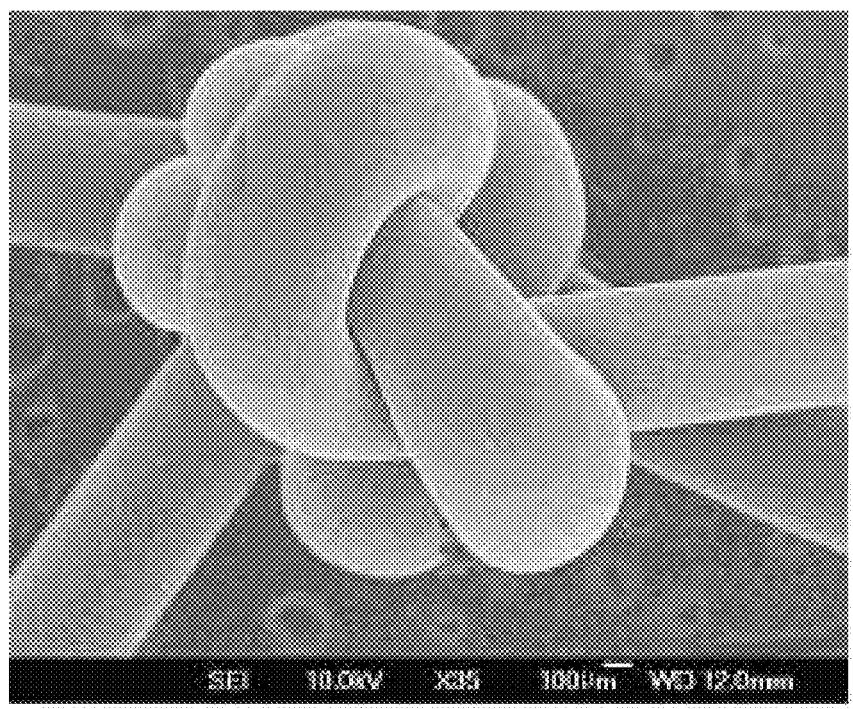
FIG. 5B is an SEM image showing the shape of the tied knot of the monofilament suture prepared by the conventional method of Comparative Example 1.

In contrast, a conventional monofilament suture spun (not conjugated spun) from a single polymer is hardly deformed during knotting and has few hills or valleys at the knotted site (see FIG. 5B). Consequently, the monofilament has a small friction coefficient of surface and the knots are easy to loose.

The present invention is further illustrated in detail by the following non-limiting examples.

EXPERIMENTAL EXAMPLE:

Evaluation of Knot security

Knot security was measured in terms of the knot slippage ratio, which is the ratio of untying of a knot when force is given. 1=1=1 knot was selected for the knot tying method.

The test was performed using a tensile strength tester (Instron Inc.). Knotting was done by applying a load amounting to 40% of the knot pull strength of absorbable monofilament suture regulated in EP and extended at a rate of 500 mm/min. The knotted sample was mounted on the tensile strength tester and the knot security thereof was measured at 50 mm of a tensile length and 50 mm/min of a tensile rate. Measurement was made 10 times for each sample. The knotted sutures were placed on a tensile strength tester and pulled apart until knot breakage occurred or the knot slipped. After ten measurements, the ratio of the number of knots slipped to the total number of the knots tied indicates the knot slippage ratio. Thus, the less the ratio is, the better the knot security of the suture. Measuring methods for the properties of the suture are summarized in Table 1.

TABLE 1

| Physical properties | Measurement methods and Instruments used |
|---|---|
| Diameter (mm) | EP standard, diameter |
| Knot pull strength (GPa) | EP standard, tensile strength, Product of Instron Inc. |
| Knot slippage ratio (%) | Surgical knot (1 = 1 = 1), Product of Instron Inc. |

Example 1

Polydioxanones with different melt indices were respectively used as components for a sea and islands, and spun to have a cross-sectional structure of conjugated filaments according to the conditions summarized in the following Table 2, to prepare a monofilament suture having a sea/islands type cross-section. Diameter, knot pull strength and knot slippage ratio of the suture were measured by the evaluation method as described above. The results are given in following Table 11.

TABLE 2

Preparation conditions for sea/islands type suture

| Suture Standard | | EP 3.5 | |
|---|---|---|---|
| Polymer | | Polydioxanone | Polydioxanone |
| Melt index (g/10 min) | | 1.9 | 1.3 |
| Processing conditions | | Spinning conditions (examples) | |
| Extruder | | Ext. 1 (islands) | Ext. 2 (sea) |
| Number of islands | | 19 | — |
| Extruder screw (rpm) | | 6.0 | 11.2 |
| Manifold pressure (kgf/cm²) | | 80 | 80 |
| Extruder temperature (° C.) | Zone 1 | 170 | 190 |
| | Zone 2 | 173 | 198 |
| | Zone 3 | 175 | 195 |
| Manifold temperature (° C.) | | 175 | 195 |
| Metering pump temperature (° C.) | | 176 | 194 |
| Nozzle pack die temperature (° C.) | | 195 | |
| Metering pump capacity (cc/rev) | | 1.2 | 1.2 |
| Metering pump revolution (rpm) | | 4.0 | 9.3 |
| Cooling bath temperature (° C.) | | 20 | |
| Undrawn yarn winding rate (m/min) | | 16.5 | |

| | Drawing conditions (example) |
|---|---|
| 1st roller (m/min) | 6.0 |
| 1st drawing oven temperature (° C.) | 110 |
| 2nd roller (m/min) | 35.0 |
| 2nd drawing oven temperature (° C.) | 115 |
| 3rd roller (m/min) | 37.3 |
| 3rd drawing oven temperature (° C.) | 115 |
| 4th roller (m/min) | 30.0 |
| Total drawing ratio | 5.00 |

Example 2

Triblock copolymers comprising p-dioxanone, trimethylene carbonate, and ε-caprolactone, having identical melt indices were spun to have a cross-sectional structure of conjugated filaments into a monofilament suture having a sea/islands type cross-section, each used as components for a sea and islands, respectively, according to the method summarized in Table 3 below. Diameter, knot pull strength, and knot slippage ratio of the obtained suture were measured by the evaluation method described above. The results are given in the following Table 11.

TABLE 3

Preparation conditions for sea/islands type suture

| Standard | | EP 4 | |
|---|---|---|---|
| Polymer | | Copolymer* | Copolymer* |
| Melt index (g/10 min) | | 4.9 | 4.9 |
| Processing conditions | | Spinning conditions (example) | |
| Extruder | | Ext. 1 (islands) | Ext. 2 (sea) |
| Number of islands | | 19 | — |
| Extruder screw (rpm) | | 8.8 | 4.2 |
| Manifold pressure (kgf/cm²) | | 80 | 80 |
| Extruder temperature (° C.) | Zone 1 | 166 | 166 |
| | Zone 2 | 168 | 168 |
| | Zone 3 | 170 | 170 |
| Manifold temperature (° C.) | | 170 | 170 |
| Metering pump temperature (° C.) | | 170 | 170 |
| Nozzle pack die temperature (° C.) | | 170 | |
| Metering pump capacity (cc/rev) | | 1.2 | 1.2 |
| Metering pump revolution (rpm) | | 7.0 | 3.0 |
| Cooling bath temperature (° C.) | | 21 | |
| Undrawn yarn winding rate (m/min) | | 9.9 | |

TABLE 3-continued

Preparation conditions for sea/islands type suture

| | Drawing conditions (example) |
|---|---|
| 1st roller (m/min) | 5.4 |
| 1st drawing oven temperature (° C.) | 90 |
| 2nd roller (m/min) | 26.4 |
| 2nd drawing oven temperature (° C.) | 95 |
| 3rd roller (m/min) | 27.9 |
| 3rd drawing oven temperature (° C.) | 95 |
| 4th roller (m/min) | 25.0 |
| Total drawing ratio | 4.63 |

*Triblock copolymer composed of p-dioxanone, trimethylene carbonate and ε-caprolactone Example 3

Nylon 6 polymers having identical melt indices were spun to have a cross-sectional structure of conjugated filaments into a monofilament suture having a sea/islands type cross-section, each used as components for a sea and islands, respectively, according to the method summarized in Table 4 below. Diameter, knot pull strength and knot slippage ratio of the suture were measured by the evaluation method described above. The results are given in Table 11.

TABLE 4

Preparation conditions for sea/islands type suture

| Standard | EP 5 | |
|---|---|---|
| Polymer | Nylon 6 | Nylon 6 |
| Melt index (g/10 min) | 5.2 | 5.2 |

| Processing conditions | Spinning conditions (example) | |
|---|---|---|
| Extruder | Ext. 1 (islands) | Ext. 2 (sea) |
| Number of islands | 8 | — |
| Extruder screw (rpm) | 14.5 | 20.6 |
| Manifold pressure (kgf/cm²) | 80 | 80 |
| Extruder temperature (° C.) Zone 1 | 219 | 218 |
| Zone 2 | 240 | 232 |
| Zone 3 | 250 | 250 |
| Manifold temperature (° C.) | 249 | 251 |
| Metering pump temperature (° C.) | 248 | 248 |
| Nozzle pack die temperature (° C.) | 250 | |
| Metering pump capacity (cc/rev) | 1.2 | 1.2 |
| Metering pump revolution (rpm) | 4.5 | 10.5 |
| Cooling bath temperature (° C.) | 34 | |
| Undrawn yarn winding rate (m/min) | 18.0 | |

| | Drawing conditions (example) |
|---|---|
| 1st roller (m/min) | 6.0 |
| 1st drawing oven temperature (° C.) | 115 |
| 2nd roller (m/min) | 24.7 |
| 2nd drawing oven temperature (° C.) | 115 |
| 3rd roller (m/min) | 25.3 |
| 3rd drawing oven temperature (° C.) | 115 |
| 4th roller (m/min) | 24.0 |
| Total drawing ratio | 4.00 |

Example 4

Polycaprolactones having identical melt indices were spun to have a cross-sectional structure of conjugated filaments into a monofilament suture having a sea/islands type cross-section, each used for a sea and islands, respectively, according to the method summarized in Table 5 below. Diameter, knot pull strength, and knot slippage ratio of the suture were measured by the evaluation method described above. The results are given in Table 11.

TABLE 5

Preparation conditions for sea/islands type suture

| Standard | EP 3.5 | |
|---|---|---|
| Polymer | Polycaprolactone | Poly-caprolactone |
| Melt index (g/10 min) | 2.5 | 2.5 |

| Processing conditions | Spinning conditions (example) | |
|---|---|---|
| Extruder | Ext. 1 (islands) | Ext. 2 (sea) |
| Number of islands | 8 | — |
| Extruder screw (rpm) | 4.2 | 9.3 |
| Manifold pressure (kgf/cm²) | 80 | 80 |
| Extruder temperature (° C.) Zone 1 | 185 | 185 |
| Zone 2 | 188 | 190 |
| Zone 3 | 180 | 190 |
| Manifold temperature (° C.) | 190 | 190 |
| Metering pump temperature (° C.) | 194 | 195 |
| Nozzle pack die temperature (° C.) | 195 | |
| Metering pump capacity (cc/rev) | 1.2 | 1.2 |
| Metering pump revolution (rpm) | 3.0 | 7.0 |
| Cooling bath temperature (° C.) | 24 | |
| Undrawn yarn winding rate (m/min) | 10.9 | |

| | Drawing conditions (example) |
|---|---|
| 1st roller (m/min) | 5.5 |
| 1st drawing oven temperature (° C.) | 75 |
| 2nd roller (m/min) | 36.6 |
| 2nd drawing oven temperature (° C.) | 80 |
| 3rd roller (m/min) | 37.2 |
| 3rd drawing oven temperature (° C.) | 80 |
| 4th roller (m/min) | 30.0 |
| Total drawing ratio | 5.45 |

Example 5

Polydioxanones having identical melt indices were spun to have a cross-sectional structure of conjugated filaments into a monofilament suture having a sea/islands type cross-section, each used for a sea and islands, respectively, according to the method summarized in Table 6 below. Diameter, knot pull strength, and knot slippage ratio of the suture were measured by the evaluation method described above. The results are given in Table 11.

TABLE 6

Preparation conditions for sea/islands type suture

| Standard | EP 3.5 | |
|---|---|---|
| Polymer | Polydioxanone | Polydioxanone |
| Melt index (g/10 min) | 1.9 | 1.9 |

| Processing conditions | Spinning conditions (example) | |
|---|---|---|
| Extruder | Ext. 1 (islands) | Ext. 2 (sea) |
| Number of islands | 37 | — |
| Extruder screw rpm | 11.4 | 5.6 |
| Manifold pressure (kgf/cm²) | 80 | 80 |
| Extruder temperature (° C.) Zone 1 | 190 | 180 |
| Zone 2 | 195 | 184 |
| Zone 3 | 195 | 185 |
| Manifold temperature (° C.) | 195 | 185 |
| Metering pump temperature (° C.) | 192 | 186 |
| Nozzle pack die temperature (° C.) | 195 | |
| Metering pump capacity (cc/rev) | 1.2 | 1.2 |
| Metering pump revolution (rpm) | 9.3 | 4.0 |
| Cooling bath temperature (° C.) | 21 | |
| Undrawn yarn winding rate (m/min) | 13.9 | |

| | Drawing conditions (example) |
|---|---|
| 1st roller (m/min) | 4.8 |
| 1st drawing oven temperature (° C.) | 110 |

TABLE 6-continued

| Preparation conditions for sea/islands type suture | |
|---|---|
| 2nd roller (m/min) | 29.8 |
| 2nd drawing oven temperature (° C.) | 120 |
| 3rd roller (m/min) | 31.7 |
| 3rd drawing oven temperature (° C.) | 120 |
| 4th roller (m/min) | 25.0 |
| Total drawing ratio | 5.21 |

Comparative Example 1

A conventional monofilament suture was prepared from polydioxanone by the method summarized in Table 7 below. Diameter, knot pull strength, and knot slippage ratio of the suture were measured by the evaluation method described above. The results are given in Table 11.

TABLE 7

| Preparation conditions for monofilament suture | | |
|---|---|---|
| Standard | | EP 4 |
| Polymer | | Polydioxanone |
| Melt index (g/10 min) | | 1.9 |
| Processing conditions | | Spinning conditions (example) |
| Extruder screw rpm | | 11.4 |
| Manifold pressure (kgf/cm$^2$) | | 80 |
| Extruder temperature (° C.) | Zone 1 | 170 |
| | Zone 2 | 177 |
| | Zone 3 | 175 |
| Manifold temperature (° C.) | | 175 |
| Metering pump temperature (° C.) | | 175 |
| Nozzle pack die temperature (° C.) | | 195 |
| Metering pump capacity (cc/rev) | | 1.2 |
| Metering pump revolution (rpm) | | 9.3 |
| Cooling bath temperature (° C.) | | 22 |
| Undrawn yarn winding rate (m/min) | | 10.3 |
| | | Drawing conditions (example) |
| 1st roller (m/min) | | 6.3 |
| 1st drawing oven temperature (° C.) | | 110 |
| 2nd roller (m/min) | | 35.0 |
| 2nd drawing oven temperature (° C.) | | 115 |
| 3rd roller (m/min) | | 37.3 |
| 3rd drawing oven temperature (° C.) | | 115 |
| 4th roller (m/min) | | 30.0 |
| Total drawing ratio | | 4.76 |

Comparative Example 2

A conventional monofilament suture was prepared from a triblock copolymer composed of p-dioxanone, trimethylene carbonate and ε-caprolactone by the method summarized in Table 8 below. Diameter, knot pull strength, and knot slippage ratio of the suture were measured by the evaluation method described above. The results are given in Table 11.

TABLE 8

| Preparation conditions for monofilament suture | |
|---|---|
| Standard | EP 4 |
| Polymer | Copolymer |
| Melt index (g/10 min) | 4.9 |

TABLE 8-continued

| Preparation conditions for monofilament suture | | |
|---|---|---|
| Processing conditions | | Spinning conditions (example) |
| Extruder screw rpm | | 11.9 |
| Manifold pressure (kgf/cm$^2$) | | 80 |
| Extruder temperature (° C.) | Zone 1 | 170 |
| | Zone 2 | 172 |
| | Zone 3 | 174 |
| Manifold temperature (° C.) | | 175 |
| Metering pump temperature (° C.) | | 175 |
| Nozzle pack die temperature (° C.) | | 175 |
| Metering pump capacity (cc/rev) | | 1.2 |
| Metering pump revolution (rpm) | | 8.5 |
| Cooling bath temperature (° C.) | | 21 |
| Undrawn yarn winding rate (m/min) | | 7.5 |
| | | Drawing conditions (example) |
| 1st roller (m/min) | | 5.4 |
| 1st drawing oven temperature (° C.) | | 90 |
| 2nd roller (m/min) | | 26.4 |
| 2nd drawing oven temperature (° C.) | | 95 |
| 3rd roller (m/min) | | 27.9 |
| 3rd drawing oven temperature (° C.) | | 95 |
| 4th roller (m/min) | | 25.0 |
| Total drawing ratio | | 4.63 |

Comparative Example 3

A conventional monofilament suture was prepared from nylon 6 by the method summarized in Table 9 below. Diameter, knot pull strength, and knot slippage ratio of the suture were measured by the evaluation method described above. The results are given in Table 11.

TABLE 9

| Preparation conditions for monofilament suture | | |
|---|---|---|
| Standard | | EP 5 |
| Polymer | | Nylon 6 |
| Melt index (g/10 min) | | 5.2 |
| Processing conditions | | Spinning conditions (example) |
| Extruder screw rpm | | 26.8 |
| Manifold pressure (kgf/cm$^2$) | | 80 |
| Extruder temperature (° C.) | Zone 1 | 219 |
| | Zone 2 | 233 |
| | Zone 3 | 250 |
| Manifold temperature (° C.) | | 249 |
| Metering pump temperature (° C.) | | 250 |
| Nozzle pack die temperature (° C.) | | 250 |
| Metering pump capacity (cc/rev) | | 1.2 |
| Metering pump revolution (rpm) | | 15.0 |
| Cooling bath temperature (° C.) | | 34 |
| Undrawn yarn winding rate (m/min) | | 18.0 |
| | | Drawing conditions (example) |
| 1st roller (m/min) | | 6.0 |
| 1st drawing oven temperature (° C.) | | 115 |
| 2nd roller (m/min) | | 24.7 |
| 2nd drawing oven temperature (° C.) | | 115 |
| 3rd roller (m/min) | | 25.3 |
| 3rd drawing oven temperature (° C.) | | 115 |
| 4th roller (m/min) | | 24.0 |
| Total drawing ratio | | 4.00 |

Comparative Example 4

A conventional monofilament suture was prepared from polycaprolactone by the method summarized in Table 10 below. Diameter, knot pull strength, and knot slippage ratio of the suture were measured by the evaluation method described above. The results are given in Table 11.

TABLE 10

Preparation conditions for monofilament suture

| Standard | EP 3.5 |
|---|---|
| Polymer | Polycaprolactone |
| Melt index (g/10 min) | 2.5 |

| Processing conditions | Spinning conditions (example) |
|---|---|
| Extruder screw rpm | 9.3 |
| Manifold pressure (kgf/cm$^2$) | 80 |
| Extruder temperature (° C.) Zone 1 | 175 |
| Zone 2 | 178 |
| Zone 3 | 180 |
| Manifold temperature (° C.) | 180 |
| Metering pump temperature (° C.) | 180 |
| Nozzle pack die temperature (° C.) | 180 |
| Metering pump capacity (cc/rev) | 1.2 |
| Metering pump revolution (rpm) | 7.0 |
| Cooling bath temperature (° C.) | 21 |
| Undrawn yarn winding rate (m/min) | 8.8 |

| | Drawing conditions (example) |
|---|---|
| 1st roller (m/min) | 5.3 |
| 1st drawing oven temperature (° C.) | 75 |
| 2nd roller (m/min) | 36.3 |
| 2nd drawing oven temperature (° C.) | 80 |
| 3rd roller (m/min) | 37.2 |
| 3rd drawing oven temperature (° C.) | 80 |
| 4th roller (m/min) | 30.0 |
| Total drawing ratio | 5.66 |

Physical properties of the sutures prepared in Examples 1 to 5 and Comparative Examples 1 to 4 are summarized in Table 11 below.

TABLE 11

| | Examples | | | | | Comparative Examples | | | |
|---|---|---|---|---|---|---|---|---|---|
| | 1 | 2 | 3 | 4 | 5 | 1 | 2 | 3 | 4 |
| Standard | EP3.5 | EP4 | EP5 | EP3.5 | EP3.5 | EP4 | EP4 | EP5 | EP3.5 |
| Diameter (mm) | 0.462 | 0.544 | 0.500 | 0.477 | 0.493 | 0.501 | 0.589 | 0.503 | 0.437 |
| Knot strength (GPa) | 0.28 | 0.22 | 0.24 | 0.32 | 0.24 | 0.24 | 0.17 | 0.24 | 0.35 |
| Knot slippage ratio (%) | 0 | 10 | 30 | 60 | 20 | 80 | 60 | 70 | 100 |

As seen in Table 11, from the comparison of the properties of Examples 1 to 5 and Comparative Examples 1 to 4, it is found that the monofilament sutures prepared so as to have a cross-sectional surface of conjugated filaments obtained by spinning had significantly improved knot security over those prepared by the conventional method such as Comparative Examples 1 to 4.

For example, the monofilament sutures of Examples 1 and 5 and Comparative Example 1 were prepared from polydioxanone. When the monofilament suture was prepared from polydioxanone by the conventional method as in Comparative Example 1, knot security was poor with the knot slippage ratio being 80%. In contrast, when the monofilament was prepared from polydioxanone to have a cross-sectional surface of conjugated filaments obtained by spinning, as in Examples 1 and 5, knot security was significantly improved with the knot slippage ratio being 0 or 20%.

Examples 1 and 5 illustrate the sutures prepared so as to have a cross-sectional surface of conjugated filaments obtained by spinning, wherein Example 1 employs polymers with different melt viscosities (melt index) but identical in other inherent properties, and Example 5 employs polymers with identical inherent properties including melt viscosity. It is seen that better knot security can be achieved when polymers having different melt viscosities are used, as in Example 1, due to the more distinct interfaces generated between the first polymer and the second polymer.

When comparing Comparative Examples 2 to 4 with Examples 2 to 4, knot security was poor when the suture was prepared from a triblock copolymer comprising p-dioxanone, trimethylene carbonate and ε-caprolactone, nylon 6 or polycaprolactone according to the conventional methods as in Comparative Examples 2 to 4, with the knot slippage ratio being 60%, 70%, and 100% respectively. In contrast, knot security was significantly improved when the monofilament suture was prepared so as to have a cross-sectional surface of conjugated filaments obtained by spinning, even using the same polymers, with the knot slippage ratio being 10%, 30% and 60% respectively.

Figure 4:
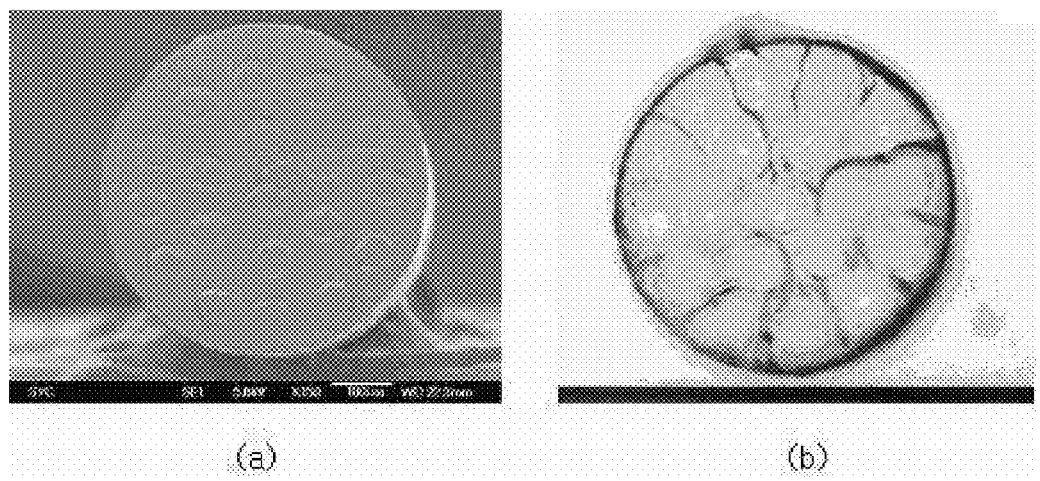
FIG. 4 shows cross-sectional views of the monofilament sutures prepared in Examples 1 and 2 of the present invention, wherein (a) is an SEM image of the monofilament suture prepared in Example 1, and (b) is an optical microscopic image of the monofilament suture prepared in Example 2.

FIG. 4 shows the cross-sections of the monofilament sutures prepared in Examples 1 and 2. FIG. 4(a) shows an SEM image of the monofilament suture prepared in Example 1 and FIG. 4(b) is an optical microscopic image (Differential Interference Contrast (DIC) micrograph) of the monofilament suture prepared in Example 2. As seen in this figure, the monofilament suture prepared by spinning to have a cross-sectional surface of conjugated filaments has distinct interfaces like in conjugated filaments, and thereby each component is well distinguished.

FIG. 5A and FIG. 5B are SEM images for comparing knot configuration of the sutures. FIG. 5A shows the knot of the monofilament suture prepared in Example 1 which has a cross-section of a sea/islands type, and FIG. 5B shows the knot of the monofilament suture prepared in Comparative Example 1 by the conventional method. As seen in FIG. 5A, the suture of the present invention is deformed to generate hills and valleys during knot tying, which significantly increases the friction coefficient of the suture at the knotted site. In contrast, in the suture shown in FIG. 5B, smaller deformation occurs and few hills and valleys are generated during knot tying, with the result that the suture has a small friction coefficient at the knotted site and the knots are easy to loose.

Example 6

A monofilament suture having a sea/islands type cross-section was spun in the same manner as in Example 1, except that a D&C Violet No.2 dye was added to the polymers forming the sea part and/or the island parts with the content given in Table 12 below (the dye content is based on 100 parts by weight of the polymer). The degree of dye bleeding was measured after the spinning was completed.

The dye was extracted from the suture with acetone of 1 g/25 mL at room temperature for about 1 minute, and then, UV absorbance was measured at 576 nm, to quantify the degree of dye bleeding. The results are given in Table 12.

TABLE 12

| Dye content (parts by weight) | | |
|---|---|---|
| Sea part | Island parts | Degree of dye bleeding (ppm) |
| 0.07 | 0.07 | 70 |
| 0.03 | 0.07 | 7 |
| 0 | 0.07 | ≤1 |

As apparent from the above description, the present invention provides a novel monofilament suture having improved knot security, as well as a smooth surface causing little tissue damage, and no voids found in the conventional multifilament sutures causing little microbial infection due to capillary action, etc.

Also, the monofilament suture of the present invention may be widely used in the medical field for ligatures, artificial ligaments, soft tissue patches, surgical meshes, thin film type dressings, surgical felts, artificial blood vessels, artificial skins, sternum tapes, etc., as well as for sutures.

While the present invention has been described with reference to the preferred embodiments, it will be understood by those skilled in the art that various modifications in form and detail may be made without departing from the scope and spirit of the invention. Accordingly, modifications such as those suggested above, but not limited thereto, are to be considered within the scope of the present invention.

What is claimed is:

1. A method for improving knot security of a monofilament suture, comprising separately melting a first polymer and a second polymer having identical chemical composition and identical inherent properties selected from melting point, density, and modulus of elasticity and spinning them into a monofilament having a cross-sectional structure of conjugated filaments, and the first polymer and the second polymer are different in melt viscosity, wherein both the first and second polymers are bioabsorbable or non-bioabsorbable, wherein the cross-section has a sea/islands type structure, and wherein the difference of the melt viscosity of the first polymer and the second polymer is at least 10%.

2. The method according to claim 1, wherein the ratio between the first polymer and the second polymer is 5:95 to 95:5 by volume.

3. The method according to claim 1, wherein the ratio between the first polymer and the second polymer is 20:80 to 80:20 by volume.

4. The method as set forth in claim 1, wherein the bioabsorbable polymer is a homopolymer or a copolymer comprising one or more selected from the group consisting of glycolide, glycolic acid, lactide, lactic acid, caprolactone, dioxanone, trimethylene carbonate, polyethylene glycol, polyanhydride, and polyhydroxyalkanoate.

5. The method as set forth in claim 1, wherein the non-bioabsorbable polymer is a homopolymer or a copolymer comprising one or more selected from the group consisting of polyolefin, polyamide, polyurethane and polyvinylidene fluoride.

6. The method according to claim 1, wherein a dye is added in the amount of 0.5 parts by weight or less on the basis of 100 parts by weight of the polymer.

7. The method according to claim 1, wherein a dye is added in the amount of 0.5 parts by weight or less on the basis of 100 parts by weight of the polymer, the pigment content being expressed by the following equation:

$$0 \leq \frac{\text{Dye content in the Sea}}{\text{Dye content in the Islands}} < 1.$$

8. The method according to claim 7, wherein the pigment is added only to the polymer forming the islands of the sea/islands type structure.

9. The method according to claim 1, wherein the first and second polymers are both non-bioabsorbable.

* * * * *